United States Patent [19]

Noiles

[11] 3,999,537
[45] Dec. 28, 1976

[54] TEMPERATURE, PULSE AND RESPIRATION DETECTOR

[75] Inventor: Douglas G. Noiles, New Canaan, Conn.

[73] Assignee: United States Surgical Corporation, New York, N.Y.

[22] Filed: Oct. 25, 1973

[21] Appl. No.: 409,637

[52] U.S. Cl. .............................. 128/2 R; 128/2 H; 128/DIG. 29; 73/344

[51] Int. Cl.² ........................................ A61B 5/00

[58] Field of Search ...... 128/2 H, 2 R, 2 C, 2.05 R, 128/2.08, DIG. 29, 2 E; 73/344, 204, 361, 359

[56] References Cited

UNITED STATES PATENTS

| | | | |
|---|---|---|---|
| 1,942,516 | 1/1934 | Noyes, Jr. | 73/359 |
| 3,081,765 | 3/1963 | Kompelien | 128/2 H |
| 3,215,265 | 11/1965 | Welin-Berger | 128/2 H |
| 3,513,832 | 5/1970 | Klemm et al. | 128/2.05 R |
| 3,531,992 | 10/1970 | Moore | 73/359 |
| 3,572,322 | 3/1971 | Wade | 128/DIG. 29 |
| 3,593,704 | 7/1971 | Schwab | 128/2 H |
| 3,645,133 | 2/1972 | Simeth | 128/DIG. 29 |
| 3,688,580 | 9/1972 | Jarzembski | 73/361 |
| 3,884,219 | 5/1975 | Richardson et al. | 128/2 R |
| 3,916,877 | 11/1975 | Beckman | 128/2.05 R |
| 3,935,744 | 2/1976 | Beckman | 73/361 |

OTHER PUBLICATIONS

Gundersen, "Reg. of Breathing Rate with Twin Thermocouples", Proceeding of the 1st Norelic Meeting on Med. & Bio Eng'g., pp. 158-160, Jan. 1970.
Gundersen, "Therm. Amp. for . . . Temp.", Med. & Bio..Eng., vol. 10, pp. 564-566, Dec. 1971.

*Primary Examiner*—Robert W. Michell
*Assistant Examiner*—Lee S. Cohen
*Attorney, Agent, or Firm*—Fleit & Jacobson

[57] ABSTRACT

A temperature, pulse and respiration detector is disclosed having a disposable oral probe with a thermopile mounted thereon. The thermopile comprises a plurality of hot junctions mounted near one end of the probe for insertion into the mouth. These hot junctions act as a temperature sensor and as one of the electrodes for pulse detection. The thermopile also comprises at least one hot junction spaced from the end of the probe for sensing nasal respiration. The other pulse detection electrode is mounted on a connector housing which holds the disposable probe. In use, the patient holds the connector housing with his left hand so that his thumb contacts the electrode mounted thereon and places the probe in his mouth. The patient's temperature and respiration are sensed by the thermopile and his pulse rate derived from the electrical activity of the heart sensed by the electrodes.

16 Claims, 8 Drawing Figures

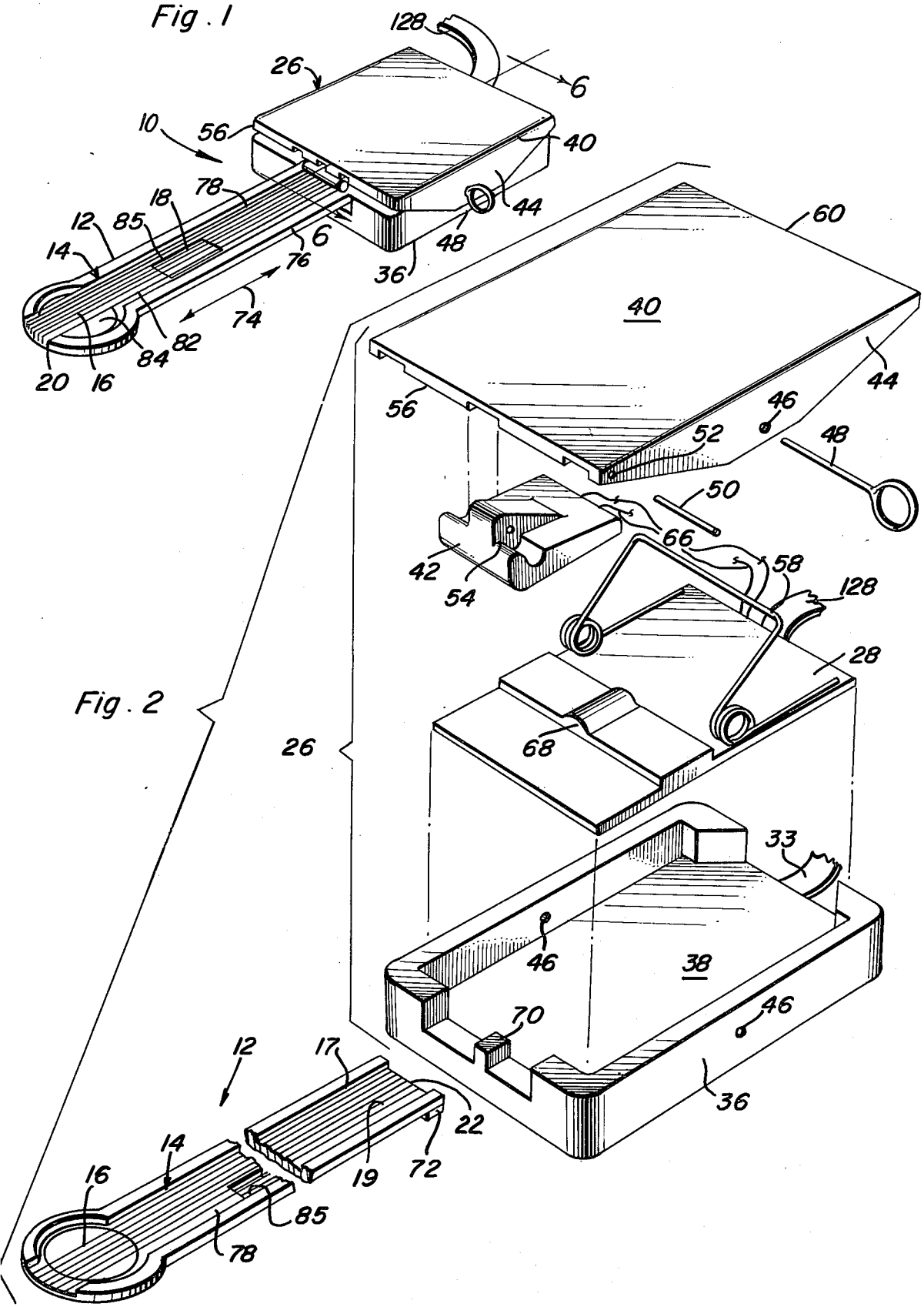

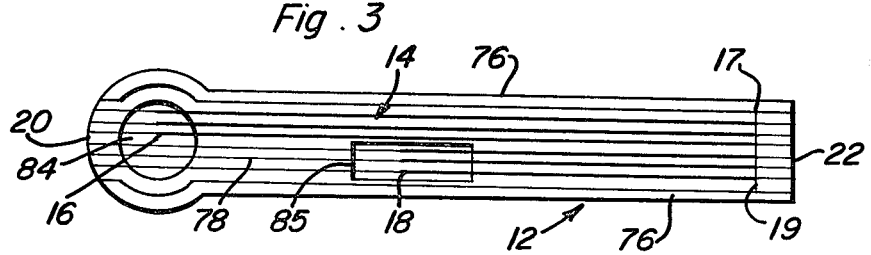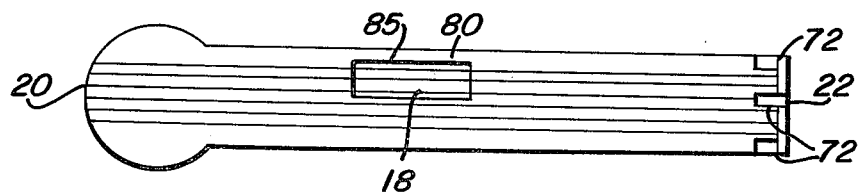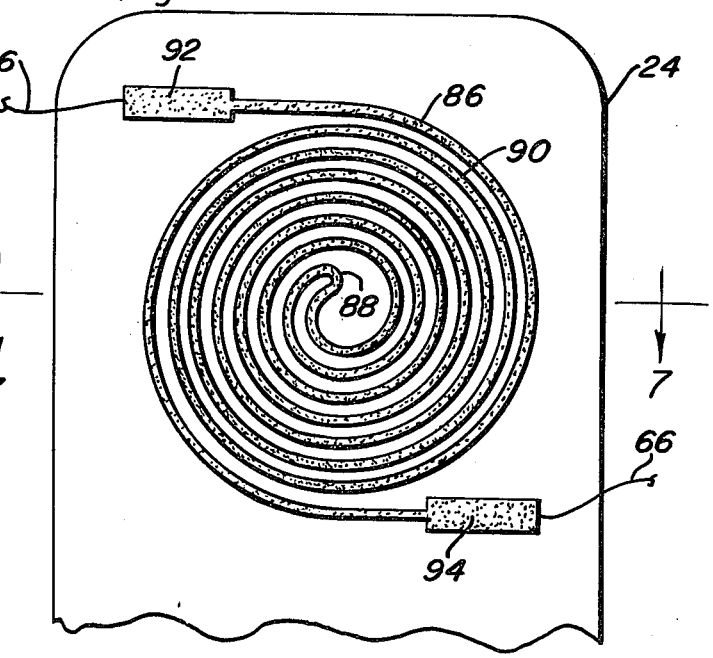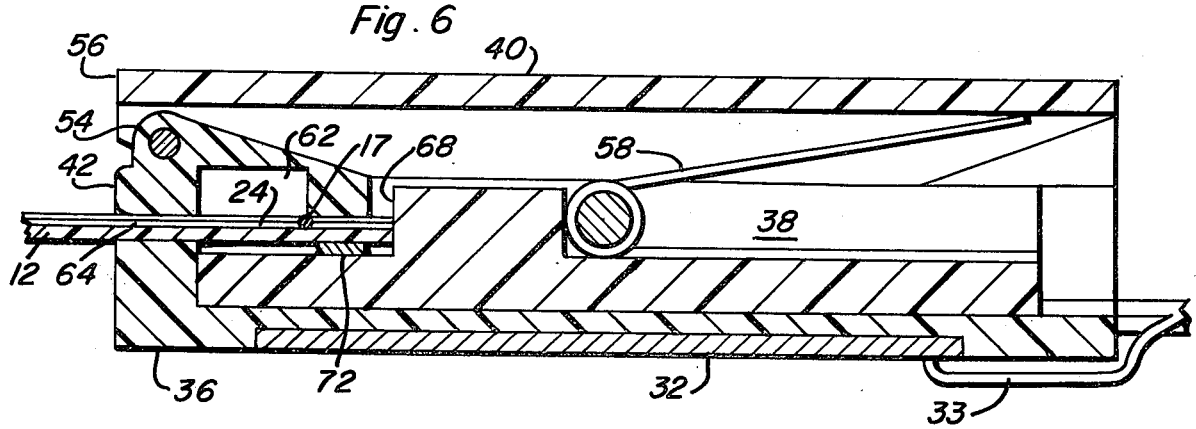

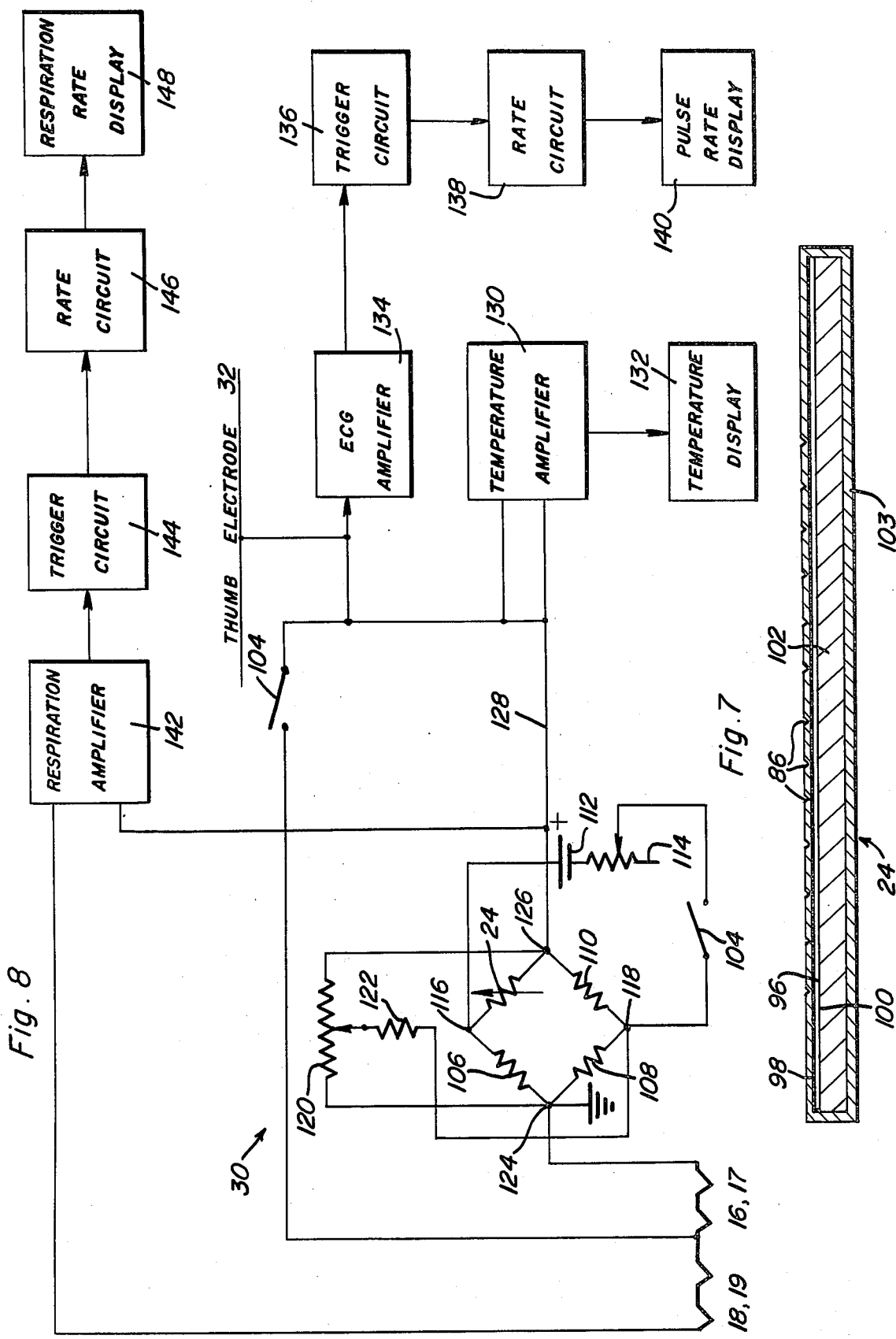

TEMPERATURE, PULSE AND RESPIRATION DETECTOR

CROSS-REFERENCE TO RELATED APPLICATIONS

This application is related to application Ser. No. 409,382, for "Temperature and Pulse Detector", by Paul Beckman, filed Oct. 25,1973, now U.S. Pat. No. 3,916,817 and his earlier application Ser. No. 398,327, filed Sept. 18, 1973, for "Clinical Thermometer" now U.S. Pat. No. 3,935,744, which is a continuation-in-part of his application Ser. No. 324,015, filed Jan. 16, 1973, now abandoned.

BACKGROUND OF THE INVENTION

This invention relates to a temperature, pulse and respiration detector. More particularly, this invention relates to a combined temperature, pulse and respiration detector in which a patient's oral temperature and pulse and respiration rates can be determined simultaneously.

It is well known to use a temperature sensor such as a thermocouple to sense oral temperature or to measure the changes of temperature between inspired and expired air and thereby detect respiration. However, suitable means for simultaneously detecting oral temperature and respiration by means of the temperature difference betwen inspired and expired air has not been developed.

It is also well known to use electrodes for detecting the electrical activity of the heart for the purpose of obtaining an electrocardiogram (EGG) and for measuring heart rate. With each heart beat, an electrical impulse passes through the heart resulting in the rhythmic contraction of the heart muscle. As the impulse passes through the heart, electrical currents spread into the tissue surrounding the heart, and a small portion of these spread all the way to the surface of the body. If electrodes are placed on the body on opposite sides of the heart, the electrical potentials generated by the heart can be sensed and recorded.

The ECG waveform contains several distinct characteristics generally labeled P, Q, R, S and T. Each ECG waveform represents one heart beat. The QRS portion or "R-wave" is the portion of the waveform normally used to trigger heart rate monitors. The R-wave has high amplitude and short duration and is made up of the highest frequency componets of the ECG waveform. Accordingly, the R-wave can be further accentuated over the P and T waves by the use of a high pass filter or waveform differentiation circuit. The heart rate is then derived from the time duration between R-waves.

Metal plates are typically used as the electrodes for detecting the electrical activity of the heart. These electrode plates are normally strapped to various parts of the body with some type conductive paste or gel applied to the skin under the plate. Other forms of electrodes include metal dust and adhesive coated on the body with a lead wire embedded therein. In either case, however, the mounting of the electrodes on the body is time consuming and unpleasant for the patient.

The simultaneous detection of temperature, pulse and respiration is highly desirable since it results in considerable time saving and a reduction in hospital costs. Prior art systems have been developed for simultaneously sensing these three parameters but these systems typically employ the use of a transducer assembly attached to the body. These prior art systems are complex since they employ devices which must be semi-permanently attached to the body and do not lead to savings in time or reduction in hospital operating costs.

SUMMARY OF THE INVENTION

An object of the present invention is to provde an improved apparatus for simultaneously sensing temperature and respiration.

Another object of the present invention is to provide a temperature and respiration detector in which the temperature and respiration sensing means are mounted on a disposable probe.

Still another object of the present invention is to provide an improved apparatus for simultaneously sensing temperature, pulse and respiration.

Yet another object of the present invention is to provide a temperature, pulse and respiration detector in which these parameters can be detected quickly and easily.

A combined temperature, pulse and respiration detector is provided in accordance with the present invention having a disposable oral probe with temperature and respiration sensors and an electrode for pulse detection mounted thereon. In accordance with one embodiment of the invention, a thermopile is mounted on the probe. The thermopile has a plurality of hot junctions mounted near one end of the probe for insertion into the mouth. These hot junctions act as the temperature sensor and as the electrode for pulse detection. The thermopile also has at least one hot junction spaced from the end of the probe for sensing nasal respiration. The other pulse detection electrode is mounted on a connector housing which holds the disposable probe. In use, the patient holds the connector housing with his left hand so that his thumb contacts the electrode mounted thereon and places the probe in his mouth. The patient's temperature and respiration are sensed by the thermopile and his pulse rate derived from the electrical activity of the heart sensed by the electrodes. With this arrangement the patient's temperature, pulse and respiration can be detected quickly and easily and without the time consuming and unpleasant attachment of the electrodes or transducers to the patient's body.

BRIEF DESCRIPTION OF THE DRAWINGS

FIG. 1 is a perspective view of the combined temperature, pulse and respiration detector system showing the probe and the connector housing;

FIG. 2 is a perspective, exploded view of the connector housing showing the insertion of the probe;

FIG. 3 is a plan view of the probe showing the upper surface;

FIG. 4 is a plan view of the probe showing the lower surface;

FIG. 5 is a plan view of the resistance thermometer mechanism;

FIG. 6 is a cross-sectional view of the connector housing, inserted probe and thumb electrode taken along line 6—6 of FIG. 1;

FIG. 7 is a cross-sectional view of the resistance thermometer mechanism of FIG. 5; and FIG. 8 is the circuit diagram of the combined temperature, pulse and respiration detector system.

DESCRIPTION OF THE PREFERRED EMBODIMENTS

Refering now to FIGS. 1, 2, 6 and 8, there is shown a combined temperature, pulse and respiration detector 10 for determining body temperature and respiration through generation of electromotive forces which can be translated into a reading in degrees of temperature and rate of respiration, respectively, and for determining pulse rate from an ECG waveform. In general, detector 10 comprises a modular system constructed to allow a temperature, pulse and respiration reading to be taken simultaneously and in a matter of seconds. Detector 10 may be utilized in hospitals or other medical centers for simultaneously taking an accurate and quick oral temperature, pulse and respiration rate reading in patients.

Detectors 10 comprises probe 12 which has thermopile 14 mounted thereon. Thermopile 14 comprises measuring or hot junctions 16 formed near first end 20 and associated cold or reference junctions 17 formed near second end 22. Thermopile 14 also comprises measuring or hot junctions 18 spaced from first end 20 and associated cold or reference junctions 19 formed near second end 22. Hot junctions 16 are connected in series with associated cold junctions 17. Hot junctions 18 are also connected in series with associated cold junctions 19. However, the thermocouples defining junctions 16, 17 are connected in parallel with the thermocouples defining junctions 18, 19 as seen in FIG. 8. Junctions 16, 17 define the temperature sensing portion of thermopile 14 and junctions 18, 19 the respiration sensing portion.

Resistance thermometer mechanism 24 is included within connector housing 26 for measuring the temperature of cold junctions 17 and 19 of thermopile 14. Thumb electrode 32 is mounted on the bottom of connector housing 26 and acts as one of the electrodes for determining pulse. Electrical circuit 30 which is partially mounted on circuit board 28 and partially within a separate housing (not shown) is shown in FIG. 8. Electrical circuit 30 measures the temperature sensed at hot junctions 16 of thermopile 14, derives the patient's pulse rate from the electrical activity of the heart sensed by thumb electrode 32 and the oral electrode comprising hot junctions 16, and measures the patient's respiration by the nasal respiration sensed at hot junctions 18 of thermopile 14. Resistance thermometer mechanism 24 compensates for fluctuations in the temperature of cold junctions 17 and 19 and forms one arm of bridge circuit 34.

Connector housing 26 provides a mechanism for housing resistance thermometer mechanism 24, circuit board 28 and thumb electrode 32 and for releasably mounting probe 12 in a predetermined position. Connector housing 26 includes connector housing base 36 having recess 38 formed therein. Circuit board 28 containing a portion of bridge circuit 34 is mounted in connector housing base 36 within recess 38. The upper portion of connector housing 26 defines a mechanism for locating resistance thermometer mechanism 24 in good physical and thermal contact with cold junctions 17 and 19 of thermopile 14 and includes upper connector housing 40 and connector housing pivot element 42.

Upper connector housing 40 has opposed longitudinal walls 44 and is pivotally connected to connector housing base 36 by inserting pivot pin 48 through pivot openings 46. Connector housing pivot element 42 is pivotally mounted to upper connector housing 40 at forward end 56 by insertion of pivot pin 50 through pivot openings 52, 54 therein, as shown in FIGS. 2 and 6. Resistance thermometer mechanism 24 is mounted on the lower surface of pivot element 42.

Spring 58 releasably secures probe 12 within connector housing 26 in a predetermined position. Spring 58 is mounted on the upper surface of circuit board 28 and bears against upper connector housing 40 near rear end 60 thus forcing forward end 56 downward toward the forward end of base 36. Manual grasping and displacement of rear end 60 of upper connector housing 40 toward base 36 permits insertion of probe 12. After probe 12 is inserted into its proper position, rear end 60 is released and probe 12 thereby mounted in the predetermined position within connector housing 26.

Resistance thermometer mechanism 24, which is mounted on the lower surface of pivot element 42, is positioned in good physical and thermal conact with cold junctions 17 and 19 when probe member 12 is inserted into connector housing 26. Pivot element 42, as shown in FIG. 2, has a cavity 62 formed in lower surface 64 thereof. Resistance thermometer mechanism 24 closes cavity 62 and is electrically connected to electrical bridge circuit 34 on circuit board 28 through appropriate electrical leads. The positioning of resistance thermometer mechanism 24 over cavity 62 permits a fast temperature response time when measuring the temperature of cold junctions 17 and 19 located on probe 12.

Stop member 68 is secured to circuit board 28 to provide accurate positioning of probe 12 within connector housing 26. Stop member 68 prevents longitudinal passage of probe 12 beyond a predetermined point during insertion of probe 12 into housing 26. Projection 70 is formed on a forward end of connector housing base 36 and contacts lower surface 80 of probe 12 after insertion of probe 12 into connector housing 26. Contacts 72 extend downward in a vertical direction from the lower surface of probe 12 and provide electrical connection between thermopile 14 and electrical circuit 30 partially mounted on circuit board 28. Connector housing base 36, upper connector housing 40 and connector housing pivot element 42 are constructed of an electrically non-conductive material such as plastic.

Probe 12 comprises an elongated member having its longitudinal dimension in the direction of arrow 74. Probe 12 includes first end 20 which is provided with an enlarged head of suitable size and shape for taking the oral temperature of a patient, and second end 22 which is adapted to be inserted into connector housing 26. Probe 12 includes a pair of side walls 76 which define upper base surface 78 therebetween on which thermopile 14 is mounted. Vertically extending side walls 76 are discontinuous at first end 20 in order to permit the wire making up thermopile 14 to be wound around probe 12 from upper surface 78 to lower surface 80. In general, probe 12 can be formed as a single piece of plastic or like material which is substantially electrically non-conductive. Probe 12 is usually at least 3 inches long and has a length of about 4 ½ inches. Thickness on the order of 65 to 75 mils has been found to be suitable.

Thermopile 14 comprises a predetermined length of wire which is wound around probe 12 in the longitudinal direction 74 as is shown in FIGS. 1–4. Wire 82 runs above top surface 78 of probe 12 and below lower surface 80. The two ends of the continuously wound wire terminate at the two outside contacts 72 which are mounted near second end 22 on lower surface 80. The middle of the three contacts 72 is used for placing the thermocouples defining junctions 16, 17 in parallel with the thermocouples defining junctions 18, 19. Wire 82 is spaced apart and is electrically insulated by air gaps between adjacent wires.

Three to 10 complete turns of wire 82 are preferably employed for forming hot junctions 16 and associated cold junctions 17. When more than ten turns are employed, the accuracy of the temperature reading is normally not improved. However, more than ten turns can be employed if desired. For example, experiments have been run with up to twenty complete turns of wire 82 for the temperature sensing portion of thermopile 14 and good temperature readings obtained. The use of only two wire turns is not desirable because of the difficulty of obtaining an accurate temperature reading. More specifically, it is very difficult to obtain a good average temperature reading when only two wire turns are employed for the temperature sensing portion of thermopile 14. The use of only one turn of wire has proved totally unsatisfactory for obtaining accurate temperature readings. More specifically, the voltage output of a single turn of wire is too low and, because of the "point" contact with the patient's body, an average temperature cannot be obtained. For example, when making an oral temperature reading, the patient's mouth may be dry resulting in a temperature reading one or two degrees higher than the actual oral temperature. Further, localized impurities in the thermocouple may result in false temperature readings when only one turn of wire is used. However, it should be stressed that accurate pulse readings can be obtained even when a single turn of wire is employed. Also, while more than one turn of wire is preferably employed for forming hot junctions 18 and associated cold junctions 19, a single turn of wire is sufficient for obtaining accurate respiration readings.

Recess 84 is formed in first end 20 of probe 12 as shown in FIGS. 1, 2 and 3. Wire 82 passes over recess 84 with hot juntions 16 being positioned over recess 84. Recess 84 provides an air gap between the surface of probe 12 and wire 82. This forms a thermal insulation barrier between wire 82 and probe 12 and results in a fast temperature response time. Recess 84 also allows hot junctions 16 to come into more intimate contact with the body, typically the patient's tongue, and to allow saliva to surround the hot junctions resulting in a quicker and more accurate temperature reading. The saliva also acts as an electrolyte permitting the accurate sensing of pulse. It should be appreciated that recess 84 can be of different size and shape and that hot junctions 16 can be thermally insulated from probe 12 in various other ways not specifically illustrated.

Aperture or hole 85 is formed in probe 12 at a point spaced from first end 20 as shown in FIGS. 1–4. Wire 82 passes over aperture 85 with hot junctions 18 being positioned over aperture 85. Aperture 85 provides an air gap between the surface of probe 12 and wire 82. This forms a thermal insulation barrier between wire 82 and probe 12 and results in a fast respiration reponse time. Aperture 85 also allows respiration air to come into more intimate contact with hot junctions 18 resulting in a more accurate respiration reading. Aperture 85 and hot junctions 18 are positioned to be in the path of the patient's nasal respiration when probe 12 is inserted in the patient's mouth. It should be appreciated that aperture 85 can be different size and shape and that hot junctions 18 can be thermally insulated from probe 12 in various other ways not specifically illustrated. For example, aperture 85 could comprise a recess similar to recess 84.

Thermopile 14, comprising wire 82, can conveniently be formed from a first metal having a second dissimilar metal plated thereon. The second dissimilar metal can be selectively plated on the first metal after the first metal has been wound around probe 12 or, alternatively, can be plated thereon before winding and selectively deplated after winding. In the drawings, the darker portion of wire 82 represents the combination of the first and second dissimilar metals and the lighter portion represents only the first metal.

As just described, thermopile 14 is made up of wire 82 which is essentially composed of two dissimilar metals. The first or base metal generally has the lower electrical conductivity of the two dissimilar metals. The first metal can be constantan or nickel, as well as tungsten, alumel, stainless steel, platinum, palladium or other such metals. The second metal generally has a higher electrical conductivity than the first metal and extends between a first plating point and a second plating point on the upper surface 78 of probe 12. Each of these plating points defines one of the hot and cold junctions 16, 18 and 17, 19, respectively. The second metal can be copper or other metal such as silver or gold which has a higher electrical conductivity. It has been found that if constantan or other base metal wire of about 1 to 5 mils in diameter is used, a copper or second metal coating of approximately 1 to 5 mils will be satisfactory. First or base metal wires of over 5 mils in diameter are difficult to wind and wires of less than 1 mil are expensive to manufacture and may not be homogenous.

The temperature of cold junctions 17 and 19 is allowed to vary as a function of atmospheric conditions. However, changes in the temperature of cold junctions 17 and 19 are compensated for by incorporating resistance thermometer mechanism 24 into electrical circuit 30 in which it forms one arm of bridge circuit 34 as shown in FIG. 8.

The principle of operation of resistance thermometer mechanisms is well known in the art. In these mechanisms, the change in resistance of a conductor with temperature change is used to measure temperature. Metals commonly used as the sensitive element in resistance thermometers are copper, platinum and nickel. Copper is particularly preferred herein because it has a positive linear temperature coefficient of resistance over the temperature range contemplated. Referring to FIGS. 5 and 7, resistance thermometer mechanism 24 comprises a bi-filar spiral 86 of copper, typically about 2.5 mils in width, having a sharp reverse turn 88 located substantially near the center of the spiral. The turns of spiral 86 do not contact each other but are spaced apart at 90 so that the turns are electrically insulated from each other. Spiral 86 has first contact end 92 and second contact end 94 as is shown in FIG. 5. Leads 66 are connected to contact ends 92 and 94 and are used for inserting thermometer mechanism 24 into bridge circuit 34. A number of well known configurations for electrical contacts 92 and 94 can be used to provide the proper electrical connections within circuit 30.

In construction, resistance thermometer mechanism 24 includes electrically non-conductive base 96 such as a plastic layer having substantially opposed planar surfaces 98 and 100, respectively. Copper spiral 86 is securely mounted on surface 98 of base 96 by any conventional technique such as conventional etching techniques used in making etched copper circuits. Thermally conductive pad 102 is mounted on surface 100 of non-conductive base 96. Pad 102 is typically made of the same material as copper spiral 86. However, any material which has a similar coefficient of expansion such as nickel, berylium, stainless steel, or gold can be used. Resistance thermometer mechanism 24 can be sheathed in a thin protective film 103 of plastic, silicon, rubber or similar material if desired. The diameter of resistance thermometer 24 is on the order of 5 millimeters, with pad 102 being on the order of three to five mils in thickness. Resistance thermometer mechanism 24 can be mounted to pivot element 42 with bi-filar spiral 86 facing toward or away from cavity 62. Further details concerning probe 12, resistance thermometer mechanism 24 and connector housing 26 are found in application Ser. No. 398,329, filed Sept. 18, 1973, for "Clinical Thermometer", now U.S. Pat. No. 3,935,744, by Paul Beckman, the disclosure of which is expressly incorporated herein by reference.

Thumb electrode 32 can be mounted on the bottom of connector housing 26 in a number of ways. For the purposes of illustration, thumb electrode 32 is shown mounted in a recess in connector housing base 36. The electrode can be attached to connector housing 26 by any suitable technique such as by the use of an epoxy adhesive. The shape of thumb electrode 32 is not critical with a circular shape being employed in accordance with present designs. Obviously, thumb electrode 32 must be sufficiently large so that good contact is made with the thumb. Although a thumb electrode has been shown, it is also possible to mount electrode 32 on the top of connector housing 25 either on the surface of upper connector housing 40 or in a suitable recess therein. If electrode 32 is mounted in this manner, it will be contacted by the index finger rather than the thumb. A usable ECG waveform can be derived from either a finger or thumb electrode. Electrode 32 can be any conventional biopotential electrode; however, a phosphor bronze electrode is presently preferred. Thumb electrode 32 is connected to the circuitry for measuring pulse by lead 33.

Circuit 30 and the electrical connections between each of the basic elements of detector 10 are shown in FIG. 8. By incorporation of resistance thermometer mechanism 24 into bridge circuit 34 in association with resistor 106, 108 and 110, an absolute temperature reading and a more accurate respiration reading can be obtained, even with a fluctuating cold junction temperature. Bridge circuits of this type are well known in the art. As is conventional, resistors 106, 108 and 110 have low temperature coefficients.

Battery 112 is placed in series in with voltage adjustment potentiometer 114, and these elements are connected to bridge circuit 34 at nodal points 116 and 118. The electrical sensitivity of bridge circuit 34 is made as nearly equal to the sensitivity of thermopile 14 as possible. This can be easily accomplished since the sensitivity of thermopile 14 is a function of the number of turns of wire 82, and since the resistance changes of copper which make up copper spiral 86 are known as a function of temperature. With these known characteristics of the system, determination of the voltage to be supplied to the bridge circuit 34 can easily be derived in a conventional manner. In actual practice, a 500 ohm voltage adjustment potentiometer 114 has been used in series with battery 112, which is approximately 1½ volts. In this manner, a voltage of approximately ½ volt is put across bridge circuit 34. Null adjustment potentiometer 120 is connected in series with resistor 122 which somewhat desensitizes potentiometer 120. By electrically connecting potentiometer 120 and resistor 122 to nodal points 124, 118 and 126 as shown in FIG. 8, the null point of bridge circuit 34 can be easily adjusted.

The connection between thermopile 14, thumb electrode 32 and the circuitry for registering temperature, pulse and respiration is made through multi-lead cable 128. Switch 104 is used to contact battery 112 to bridge circuit 34 and thermopile 14 to the temperature, pulse and respiration registering circuitry. This is done so that battery 112 is only in an "on" condition during the time that switch 104 is actuated and measurements are being taken, otherwise battery 112 would be continually on and would run down rather quickly. Alternatively, a standard 110 voltage supply could be used in which event conventional rectification and voltage regulation would be employed.

The voltage across nodes 124, 126 of the bridge circuit is proportional to the temperature measured by resistance thermometer mechanism 24. Voltage adjustment potentiometer 114 adjusts the input voltage to bridge 34 across therminals 116 and 118 so that the sensitivity of bridge circuit 34 substantially matches that of thermopile 14. Null adjustment potentiometer 120 is correspondingly set so that bridge 34 is balanced when resistance thermometer mechanism 24 is at a temperature reading which corresponds to zero voltage. Since resistance thermometer mechanism 24 is in thermal contact with the reference junctions 17 and 19 of thermopile 14, the total output voltage of bridge circuit 34 and junctions 16, 17 is proportional to the temperature of hot junctions 16 and the total output voltage of bridge circuit 34 and junctions 18, 19 is proportional to the temperature of hot junctions 18.

In use, second end 22 of probe 12 is releasably secured in connector housing 26. As previously discussed, connector housing 26 is constructed so that cold junctions 17 and 19 will be in good physical and thermal contact with resistance thermometer mechanism 24. Copper spiral 86 and cold junctions 17 and 19 will reach thermal equilibrium in about 1 or 2 seconds. The patient is then asked to hold connector housing 26 in his left hand so that his thumb contacts thumb electrode 32. The patient's right thumb may be used on the thumb electrode; however, this will result in a reduced R-wave. If desired. a conductive paste or gel can be applied to the patient's thumb to improve the electrical contact. Probe 12 is now ready to be inserted into the patient's mouth.

With the illustrated construction of probe 12, the bottom of the tongue will lie flush against hot junctions 16. In this position saliva and mucus can surround hot junctions 16 and collect in recess 84. This intimate physical contact enables hot junctions 16 to quickly reach the patient's body temperature, namely, within a matter of milliseconds. A faster temperature response time is essential to the taking of an accurate reading since the patient's oral temperature will be lowered somewhat by the relatively colder probe 12. However, this temperature change will not occur to any appreciable extent within the temperature response time of thermopile 14. Also, the saliva will act as an electrolyte and provide good electrical contact between hot junctions 16 and the patient's mouth.

After first end 20 of probe 12 is inserted into the patient's mouth switch 104 is depressed. The output of bridge circuit 34 and junctions 16, 17 which is proportional to the temperature of hot junctions 16 is amplified in conventional "temperature" amplifier 130 and the maximum temperature reading displayed on temperature display 132, which can comprise a conventional peak and hold circuit. The output signal from thumb electrode 32 and hot junctions 16 is amplified in standard ECG amplifier 134 and passed through trigger circuit 136. The output signal from trigger circuit 136, typically a Schmidt trigger, is fed through rate circuit 138 which could be an integrator associated with a timing circuit for resetting the integrator to zero or a leaky capacitor whose equilibrium voltage is proportional to pulse rate. Finally, the pulse rate is displayed on pulse rate display 140. If desired, the ECG waveform can be displayed on an oscilloscope, electrocardiograph or other device for monitoring the electrical activity of the heart.

With first end 20 of probe 12 inserted into the patient's mouth, hot junctions 18 will be positioned in the path of the patient's nasal respiration. The output of bridge circuit 34 and junctions 18, 19 which is proportional to the temperature of hot junctions 18 is amplified in conventional "respiration" amplifier 142 and the output of the amplifier passed through trigger circuit 144. The output signal from trigger circuit 144, typically a Schmidt trigger, is fed through rate circuit 146 which could be an integrator associated with a timing circuit for resetting the integrator to zero or a leaky capacitor whose equilibrium voltage is proportional to respiration rate. Finally, the respiration rate is displayed on respiration rate display 148. If desired, the respiration waveform can be displayed on an oscilloscope or other device for monitoring respiration activity.

Although only a single embodiment of the present invention has been described herein, it should be appreciated that there are many modifications falling within this scope. For example, it should be recognized that detector 10 can be used as either a temperature and respiration detector without simultaneously detecting pulse. Additionally, although a thermopile has been described which functions both as a temperature and respiration sensor, it should be recognized that a separate respiration sensor could be provided on the probe or in the connector housing for sensing respiration. Accordingly, the present invention should only be limited as defined in the appended claims.

What is claimed is:

1. An apparatus for sensing body temperature and respiration rate comprising an elongated probe having a temperature sensor mounted thereon, said probe defining an opening at a position spaced from said temperature sensor, said probe having a respiration sensor mounted in said opening so that when the probe is inserted in the mouth of a patient the temperature sensor will sense oral temperature and said opening and respiration sensor will be in the path of nasal air flow, said probe having substantially a portion between said temperature sensor and said opening adapted to be engaged by the lips of the patient so that said opening and said respiration sensor are maintained in said path of nasal air flow, and means for connecting said temperature sensor and said sensor to means for reading out said body temperature and said respiration rate.

2. An apparatus for sensing body temperature and respiration rate comprising an elongated probe having a temperature sensor mounted thereon, said probe defining an opening at a position spaced from said temperature sensor for receiving nasal respiration, said probe having a respiration sensor mounted in said opening, said probe having a non-circular cross-section between said temperature sensor and said opening adapted to be engaged by a patient's lips, and means for connecting said temperature sensor and said respiration sensor to means for reading out said body temperature and said respiration rate, said non-circular cross-section having a major axis and a minor axis, the width of said non-circular cross-section along said major axis being substantially greater than the width of said non-circular cross-section along said minor axis whereby said major axis is oriented parallel to the line of joining of said lips when said probe is inserted in the patient's mouth and said opening and respiration sensor are maintained in the path of said nasal respiration.

3. An apparatus for sensing body temperature and respiration rate comprising an elongated probe having temperature and respiration sensors mounted thereon in spaced apart positions, said probe defining an opening therein, said respiration sensor being positioned over said opening so that when said probe is inserted into the mouth of a patient the temperature sensor is positioned in the mouth to sense oral temperature and the respiration sensor and opening are positioned outside the mouth in the path of nasal air flow, said probe having a substantially flat portion between said temperature and respiration sensors to be engaged by the lips of the patient to maintain the probe steady in the patient's mouth without the possibility of rotation, said respiration sensor being mounted on said probe so that it does not project out of the profile of said probe, and means for connecting said temperature sensor and said respiration sensor to means for reading out said body temperature and said respiration rate.

4. An oral probe for use in sensing oral temperature and respiration rate comprising an elongated, electrically non-conductive member having a first end of suitable size and shape for insertion into the mouth of a patient; thermopile means mounted on said member and defining a plurality of hot junctions near said first end of said member for insertion into the mouth for sensing oral temperature, said thermopile means also defining at least one hot junction spaced from said first end and positioned to be in the path of nasal air flow when said first end of said probe is inserted into a patient's mouth, said member having a substantially flat portion between said plurality of hot junctions and said at least one hot junction adapted to be engaged by the lips of the patient so that said at least one hot junction is maintained in said path of nasal air flow, and means for connecting said thermopile means to means for reading out said oral temperature and said respiration rate.

5. The probe of claim 4 in which said thermopile means further defines a plurality of associated cold junctions near a second end of said member and in which said probe further includes a plurality of electrical contacts mounted on said member near said second end and electrically connected to said thermopile means, said second end of said member being adapted to be detachably mounted in a housing comprising at least part of a system for using the emf developed by said thermopile in determining the oral temperature and respiration rate of said patient.

6. The probe of claim 5 in which said thermopile means define at least three hot junctions near said first end which are positioned along a line which is transverse to said member and separated from one another by air gaps.

7. The probe of claim 5 in which said thermopile means defines from three to ten hot junctions near said first end and from three to ten associated cold junctions near said second end.

8. The probe of claim 7 in which said hot junctions are separated from said member by air gaps.

9. The probe of claim 5 in which said thermopile means comprises a first metal wire would around said member in the longitudinal direction thereof and a second metal joined to said first metal wire between said hot and associated cold junctions.

10. The probe of claim 9 in which said second metal is plated on said first metal wire from a first plating point defining said hot junctions to a second plating point defining said associated cold junctions.

11. The probe of claim 4 in which said member has an aperture formed thereon and spaced from said first end and in which said at least one hot junction spaced from said first end is positioned over said aperture.

12. The probe of claim 4 in which said member has an upper surface with a recess formed therein near said first end and in which said hot junctions near said first end are positioned over said recess.

13. An oral probe for use in sensing body temperature and respiration rate, comprising:
an elongated, substantially flat, electrically non-conductive member having a first end of suitable size and shape for insertion into the mouth of a patient, said member having a recess formed in said first end and an aperture spaced from said first end;
thermopile means defining a plurality of oral temperature-sensing thermocouples connected in series mounted on said member and having at least three hot junctions near said first end of said member and at least three associated cold junctions near a second end of said member, said at least three hot junctions being positioned along a line which is transverse to said member and over said recess so that said at least three hot junctions are separated from one another and from said member by air gaps;
said thermopile means also defining at least one respiration-sensing thermocouple mounted on said member and having at least one hot junction spaced from said first end of said member and at least one associated cold junction near a second end of said member, said at least one hot junction being positioned over said aperture so that said at least one hot junction is separated from said member by an air gap; and
a plurality of electrical contacts mounted on said member near said second end and electrically connected to said thermopile means so that said oral and respiration-sensing thermocouples are connected in parallel, said second end of said member being adapted to be detachably mounted in a housing comprising at least part of a system for using the emf developed by said thermopile means in determining the oral temperature and respiration rate of said patient.

14. The probe of claim 13 in which said thermopile means defines from three to ten hot junctions near said first end and from three to ten of said associated cold junctions near said second end.

15. The probe of claim 13 in which said thermopile means comprises a first metal wire wound around said member in the longitudinal direction thereof, and a second metal joined to said first metal wire between said hot and associated cold junctions.

16. The probe of claim 15 in which said second metal is placed on said first metal wire from a first plating point defining said hot junctions to a second plating point defining said associated cold junctions.

* * * * *

UNITED STATES PATENT AND TRADEMARK OFFICE
CERTIFICATE OF CORRECTION

PATENT NO. : 3,999,537
DATED : December 28, 1976
INVENTOR(S) : Douglas G. NOILES It is certified that error appears in the above—identified patent and that said Letters Patent are hereby corrected as shown below:

Claim 1, line 10, change "said probe having substantially a" to --said probe having a substantially flat--.

line 15, after "said" insert --respiration--.

Signed and Sealed this

Fifth Day of April 1977

[SEAL]

Attest:

RUTH C. MASON
*Attesting Officer*

C. MARSHALL DANN
*Commissioner of Patents and Trademarks*